Figure 1:
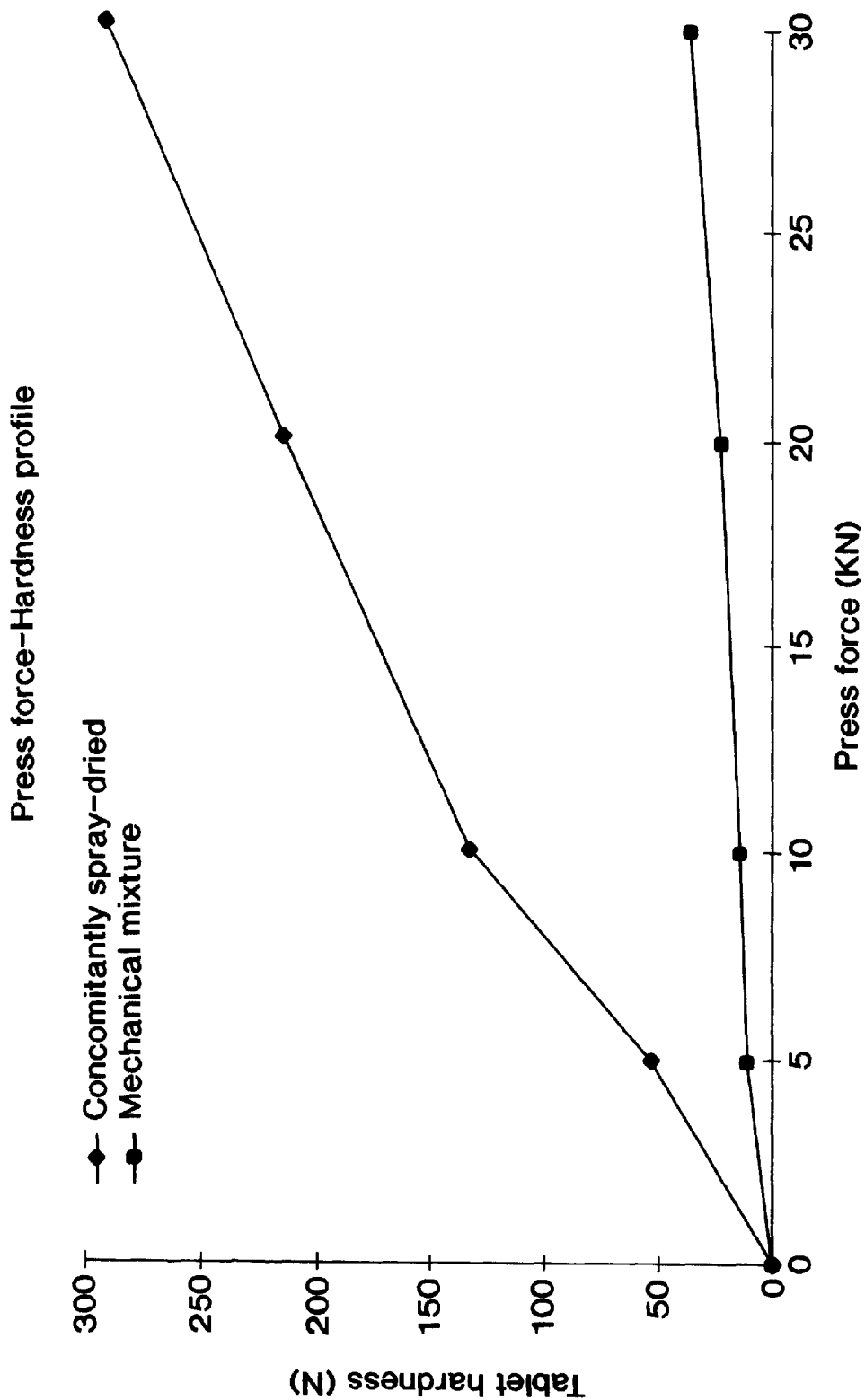
Figure 2:
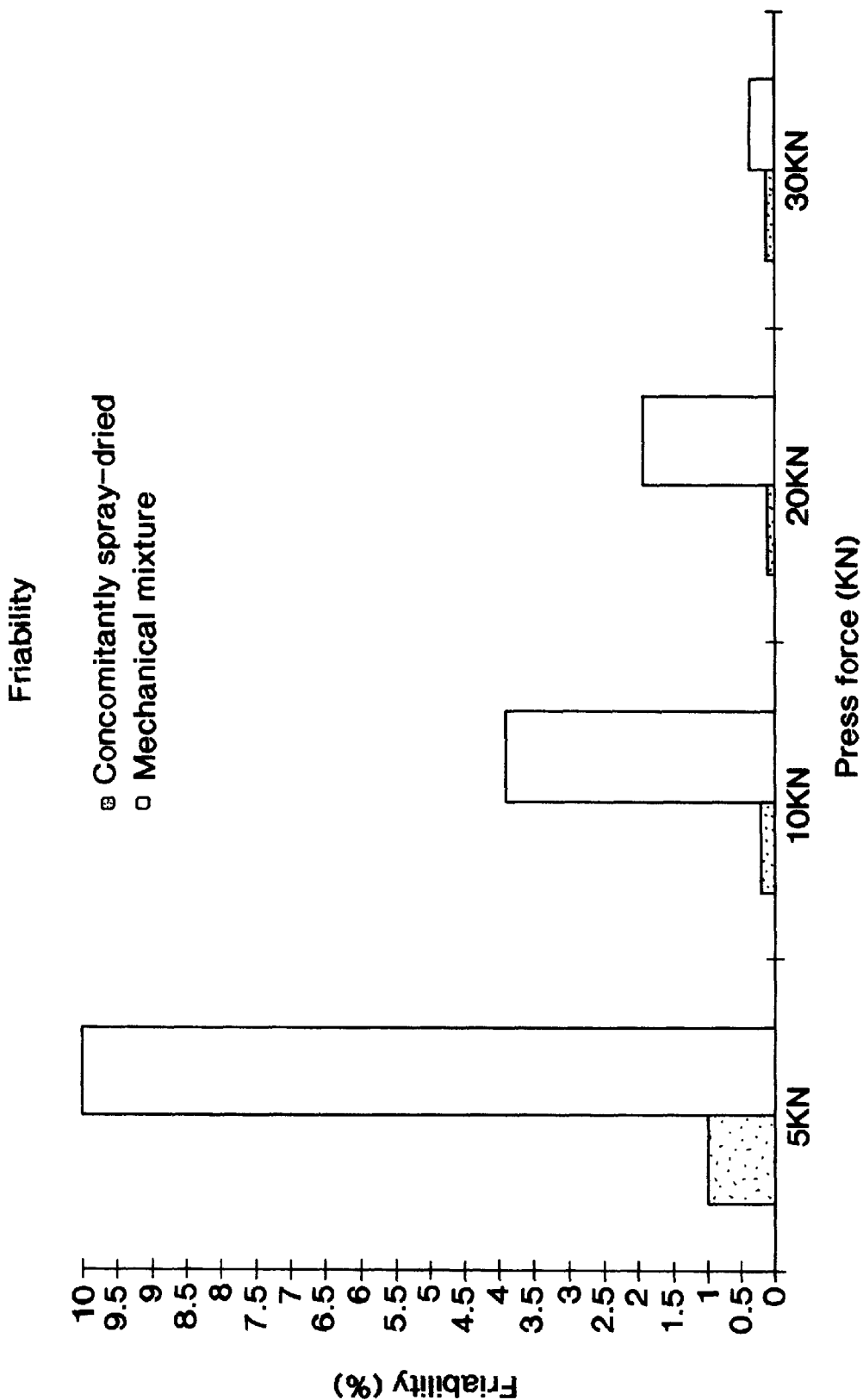

United States Patent [19]

Schwarz et al.

[11] Patent Number: 6,149,941
[45] Date of Patent: Nov. 21, 2000

[54] TASTE OF ACTIVE PHARMACEUTICAL INGREDIENTS

[75] Inventors: Eugen Schwarz, Bensheim; Gernot Möschl, Weiterstadt, both of Germany; Siva Tallavajhala, Dix Hills, N.Y.

[73] Assignee: Merck Patent Gesellschaft mit, Germany

[21] Appl. No.: 09/180,022
[22] PCT Filed: Apr. 10, 1997
[86] PCT No.: PCT/EP97/01781
  § 371 Date: Oct. 30, 1998
  § 102(e) Date: Oct. 30, 1998
[87] PCT Pub. No.: WO97/41835
  PCT Pub. Date: Nov. 13, 1997
[51] Int. Cl.[7] .................................................. A61K 9/14
[52] U.S. Cl. ............................ 424/489; 424/499; 514/774
[58] Field of Search ........................... 514/774; 424/489, 424/464, 465, 499

[56] References Cited

U.S. PATENT DOCUMENTS 4,892,889  1/1990  Kirk et al. ............................. 514/774

*Primary Examiner*—Thurman K. Page
*Assistant Examiner*—William E. Benston, Jr.
*Attorney, Agent, or Firm*—Millen, White, Zelano & Branigan, P.C.

[57] ABSTRACT

The invention relates to a process for improving the taste of solid formulations containing one or more active ingredients.

32 Claims, 2 Drawing Sheets

TASTE OF ACTIVE PHARMACEUTICAL INGREDIENTS

The invention relates to a method of improving the flavour profile of solid formulations, for example of tablets comprising active substances or mineral substances, that is to say not only the actual flavour itself but also the organoleptic sensation in the mouth.

Polyols and polyol mixtures are used on a large scale as non-cariogenic additives and excipients for, inter alia, pharmaceutically active substances, chewable tablets, lozenges and other products of the pharmaceutical industry, and as compressed articles in the food industry. As a rule, polyols are obtained by hydrogenating the sugars on which they are based. They can be obtained in solid form by crystallization or else by spray-drying. The particular advantage of some polyols is that they are also suitable for direct compression without any further auxiliaries and additives.

While the known polyols mannitol, lactitol, isomaltol and xylitol show a low degree of hygroscopicity, the tableting behaviour is poor, which results in low tablet hardness, scale-off and severe friability of the tablets. In principle, it is desired to achieve high tablet hardness since frequently only a small amount of excipients are employed in solid formulations and the active substances may drastically reduce tablet hardness so that a given pharmaceutical formula is impossible to tablet.

While lactitol, isomaltol and xylitol are less frequently used in the preparation of compressed articles, mannitol is frequently used in pharmaceutical formulations.

However, the use of mannitol entails a more complicated procedure since, as a rule, it has to be subjected to wet granulation together with the remaining ingredients of the pharmaceutical formula prior to compressing. Mannitol which can be tableted directly is also commercially available, but the hardness which can be achieved by using it is only unsatisfactory in comparison with the hardness achieved when using sorbitol.

Sorbitol, in particular sorbitol obtained by spray-drying, results in very good tablet hardness. At the same time, the compressed articles produced have particularly smooth surfaces. A paper by Basedow et al. reveals that tablets comprising calcium carbonate can be prepared by compressing with spray-dried or crystalline sorbitol. However, sorbitol shows a higher degree of hygroscopicity than the other polyols. This means that its uses are limited. In this context, there is also a lack of evidence in the literature that the flavour profile of a formulation may be improved substantially by sorbitol or by another polyol.

When formulating orally administered pharmaceutical preparations, the flavour profile perceived by the user is frequently problematic, not only in the case of liquid dosage forms. A chalky taste, in particular when chewing antacid tablets, is perceived as unpleasant. Attempts to mask this chalky taste by a wide range of additives have been relatively unsuccessful to date. Known antacids, in turn, convey an undesirable chalky, soapy taste in the mouth which can be reduced, albeit only slightly, by conventional additives, but reappears to a large extent upon chewing.

Another problem found in a wide range of active substances is a taste perceived as extremely bitter. Attempts to mask especially bitter or chalky active substances have been unsuccessful to date, even by adding flavourings or aromas. While there is a possibility of providing tablets comprising such active substances with a coating, this method is unsuitable when the aim is rapid absorption of the active substance which takes place via the mucous membrane of the mouth even while the tablets are being chewed.

The surface of tablets which are intended to be sucked, for example tablets for sore throats, also have to meet specific requirements. What is desired here is a smooth surface of the actual tablet which is retained during the sucking process and does not roughen up gradually.

Moreover, lozenges and, especially, chewable tablets are offered currently in the field of food supplements (vitamin and mineral supplements). In particular in the case of tablets for supplying minerals, the excipient amounts are very little, so that the flavour profile depends largely on the mineral in question.

It is furthermore attempted, in the production of solid formulations, increasingly to employ directly compressible active substances (DC active substances), in order to lower production costs.

It is therefore an object of the present invention to provide a method which, on the one hand, improves the flavour profile of solid formulations but which simultaneously positively affects the organoleptic sensation in the mouth of the resulting products.

It has now been found that the flavour profile of solid formulations can be improved by preparing a composition—which comprises one or more active substances and which can be obtained by concomitant spray-drying or fluidized-bed granulation with at least one polyol—in a solid dosage form by means of compressing.

The invention therefore relates to a method for the preparation of DC active substances which contribute to improving the flavour profile of solid formulations which comprise one or more active substances, characterized in that a composition—which comprises one or more active substances and can be obtained by concomitant spray-drying or fluidized-bed granulation with at least one polyol—is prepared in a solid dosage form by means of compressing. The total amount of polyol employed is to be chosen in such a way that it amounts to 10 to 90% by weight, in particular 25 to 75% by weight, of the pulverulent substance mixture prepared by the method according to the invention.

The composition which is essential to the invention can be obtained by dissolving at least one polyol in water and dissolving or suspending at least one active substance in a solvent and spraying the resulting aqueous mixture in a stream of air at a temperature of 120 to 300° C., preferably 140 to 190° C. Alternatively, it is possible to fluidize the resulting aqueous mixture in a stream of air at a temperature of 40 to 120° C.

Prior to the concomitant spray-drying or fluidized-bed granulation, flavour improvers and, if appropriate, colours may be added to the aqueous mixture. Suitable flavour improvers are, inter alia, natural or synthetic sweeteners from the group consisting of saccharin, Aspartame®, acesulfam K, neohesperidin DC, sucralose, thaumatin or stevioside. Polyols which can be employed are those from the group consisting of sorbitol, mannitol, lactitol, isomaltol, maltitol, erythritol or xylitol. These may amount to 10 to 90% by weight, in particular 25 to 75% by weight, in the resulting product.

The invention therefore also relates to the solid formulations with improved flavour profile which are produced by the method according to the invention. These formulations may comprise, on the one hand, minerals from the group of the physiologically acceptable Ca, Mg, Na, K, Fe and Zn salts in an amount of from 0.1 to 90% by weight, in particular 25 to 75% by weight, if appropriate trace elements, and one or more vitamin(s) and, if appropriate, one or more active substances which may taste bitter.

The formulations produced by the method according to the invention may comprise one or more pharmaceutically active substances. Such active substances may be, inter alia, antacids, antiallergics, analgesics, hormones, steroids, oestrogens, contraceptives, nasal decongestants, $H_1$ and $H_2$ antagonists, $\beta_2$ stimulants, vasodilators, antihypertensives, anti-infective agents, laxatives, antitussives, bronchodilators, agents against sore throats, bismuth and its salts, fungicides, antibiotics, stimulants (such as, for example, amphetamines) alkaloids, oral hypogylcaemics, diuretics, cholesterol-lowering agents, combinations of various pharmaceutically active agents or others. These active substances may amount to 0.1 to 70% by weight.

The active substances can be present as coated particles, liposomes or microparticles. Customary substances used in pharmacy can serve as a coating. The particle size of the active substances is preferably 0.1 to 800 μm with a bulk density of 0.15 to 1 g/cm³.

The percentages by weight given in the above text are, of course, to be understood in such a way that the chosen percentages of the substances employed do not exceed a total of 100.

The term polyol is to be understood as meaning sugar alcohols of the general formula $$CH_2OH\text{---}(CHOH)_n\text{---}CH_2OH,$$

n being 2 to 6, preferably 3 to 4,
and the dimeric anhydrides thereof, in particular $C_{12}H_{24}O_{11}$.

The term polyols is to be understood as meaning, in particular, hexitols such as sorbitol and mannitol, pentitols such as xylitol, but may also be $C_4$-polyalcohols such as erythritol or $C_{12}$-polyalcohols such as lactitol or maltitol. However, the term polyols is also to be understood as meaning suitable carbohydrates.

The mixture used for spray-drying is an aqueous solution of at least one polyol. Beforehand, the solids content is preferably brought to approximately 10–90% by weight, in particular 50 to 72% by weight, by mixing at least one polyol solution with one or more solutions or suspensions of the desired active substance(s) in the desired ratio at a temperature of up to 80° C. Spraying is carried out by means of atomizing using nozzles, preferably by means of a centrifugal atomizer, in a dry stream of air which is introduced centrifugally and which has been heated to a temperature of 120 to 300° C., preferably 140 to 190° C. The amount of polyol solution charged and of hot air introduced is matched in such a way that the resulting pulverulent substance mixture is dried down to a water content of approximately 0.1 to approximately 1% by weight, if appropriate in a fluidized bed. In any case, the water content should be below 1% by weight.

The fluidized-bed granulation is carried out for example as described in P. Grassmann, F. Widmer, "Einführung in die thermische Verfahrenstechnik" [Introduction to Thermal Process Technology].

The specific production process, in which an aqueous solution is sprayed, allows water-soluble additives, but also additives which are not soluble in water, for example citric acid, sweeteners, in particular acesulfam K, Aspartame®, saccharin, cyclamate, sucralose, neohesperidin DC, colours and pharmaceutically active substances, for example analgesics, antacids and the like, vitamins and, if appropriate, trace elements, to be distributed homogeneously in the solid formulation or compositions according to the invention and in the tablets prepared therefrom.

The binders which are optionally to be added are known to those skilled in the art and used to improve the hardness of the composition. Preferred binders are cellulose derivatives, in particular hydroxypropylmethylcellulose, carboxymethylcellulose or starch.

The polyol compositions characterized in this way have a series of properties which are advantageous for tableting:

Surprisingly, it is observed that solid formulations, in particular tablets, with a considerably improved flavour profile and organoleptic sensation in the mouth can be obtained by the method according to the invention with the use of the compositions according to the invention. These advantageous properties are simultaneously linked to the possibility of directly compressing the compositions obtained by concomitant spray-drying or fluidized-bed granulation. These are therefore directly compressible active substance formulations (DC active substances).

When using formulations with a high mineral content of up to 90% by weight results in dramatically improved tableting properties on the one hand and, on the other hand, the tablets produced are characterized by a considerably lower degree of friability during the packaging process. Moreover, when using the compositions according to the invention, the same pressure as is applied to known polyol-comprising formulations results in harder tablets with smoother surfaces. This improved organoleptic sensation in the mouth, which is perceived at the beginning, is also perceived during chewing or sucking since the normal chalky or even soapy flavour is masked to a high degree. Surprisingly, it is not only the flavour profile of these mineral tablets which is improved. Formulations into which extremely bitter active compounds are incorporated are perceived as considerably better tasting, since the bitter flavour is not quite so perceptible.

The examples which follow are intended to illustrate in greater detail the above invention which is described and claimed but are not suitable for restricting the scope of protection thereto.

EXAMPLES

Example 1

Antacid tablet
Composition of the tableting mixture

| | |
|---|---|
| Calcium carbonate | 65.50% |
| Karion Instant | 28.19% |
| Karion Powder P300 | 4.70% |
| Chlorophyllin 100% | 0.01% |
| Neohesperidin DC | 0.10% |
| Peppermint aroma Naefco (by Firmenich) | 0.30% |
| Maqnesium stearate | 1.00% |

Mechanical production of the mixture

Calcium carbonate and sorbitol (Karion Instant and Karion Powder P300) are mixed for 5 minutes in a Turbula mixer. Chlorophyllin, neohesperidin DC and the peppermint aroma are subsequently added and mixing is continued for 5 minutes. The mixture is passed through a screen of mesh size 1 mm. Magnesium stearate is passed through a screen of mesh size 250 μm onto the screened mixture, and mixing is continued for a further 5 minutes. The resulting mixture is tableted.

Production of the mixture by concomitant spraying

Calcium carbonate, sorbitol, neohesperidin DC and chlorophyllin are sprayed concomitantly in the manner mentioned above. The concomitantly sprayed material and the aroma are placed into a Turbula mixer, magnesium stearate is passed through a screen of mesh size 250 μm onto the mixture and everything is mixed for 5 minutes. The resulting mixture is tableted.

Results

|  | Mechanical mixture | Concomitantly sprayed material |
|---|---|---|
| Tableting (qualitative) | flowability of the mixture very poor, mould not always filled completely, tablets show scale-off | perfect tableting |
| Flow inclination angle | 37.5° | 32.6° |
| Tablet hardness | 40 N at 19 KN (maximum tablet hardness obtainable) | 129 N at approx. 8 KN |
| V$_{rel.}$ Tablet weight | not determinable | 0.19% |
| Friability (Roche) | not determinable | 0.37% |
| Organoleptic sensation | strong chalky flavour, strong chalky sensation in the mouth, very dull, weak aroma since masked by chalky flavour | readily chewable tablets, no chalky sensation in the mouth, very little chalky flavour, aroma readily recognizable |
| Active Substance Distribution | | |
| Mean value (in % of the theoretical value) | 98.2 | 99.9 |
| Deviation (min/max) | 96.0–99.8 | 99.6–100.2 |
| Deviation | 3.8% | 0.6% |

Example 2

Analgesic tablet
Composition of the tableting material

| Acetyl salicylic acid (ASA) | 74.0% |
|---|---|
| Sorbitol content | 24.5% |
| (Instant quality admixed, or sprayed with ASA) | |
| Acesulfam K | 0.5% |
| Magnesium stearate | 1.0% |

Tableting and flavour comparison
Preparation of a mechanical mixture

ASA is finely powdered by grinding and triturated with sorbitol Instant in a Turbula shaking mixer including the micronized sweetener ASK. This is followed by screening for deagglomeration using a 1 mm screen and remixing with magnesium stearate and then tableting.

Preparation of concomitantly sprayed tablet material

Finely powdered, ground ASA is partly (about 5%) introduced into the fluidized bed and the remainder is dispersed in sorbitol solution in a ratio of about 1:1. The dispersion is maintained by stirring and sprayed directly into the fluidized bed with the sweetener ASK, with simultaneous evaporation of water.

1% magnesium stearate is admixed as lubricant to the relatively fine spray granules thus formed. The mixture obtained is directly tableted.

Results

|  | Mechanical mixture | Concomitantly sprayed material |
|---|---|---|
| Appearance | only slightly flowable mixture, both main components of which are recognizable | homogeneous, readily flowable tableting granules |
| Tableting: 500 mg Press force 10 kN | | |
| Tablet hardness: | 90 N | 210 N |
| Friability | 0.6% | 0.3% |
| Organoleptic sensation | acid-dominant flavour, high surface roughness of the tablet | corrected sweetly acidic flavour, pleasant chewing behaviour (smooth, not very absorptive surface) |

Example 3

Vitamin C tablet

| Ascorbic acid | 87.7% |
|---|---|
| Sorbitol | 10.0% |
| Orange aroma (powdered) | 0.7% |
| Acesulfam K | 0.6% |
| Magnesium stearate | 1.0% |

Preparation of a mechanical mixture

The finely crystalline ascorbic acid is intimately triturated in a Turbula shaking mixer with sorbitol Instant (granulation under 0.3 mm), sweetener and aroma. The lubricant magnesium stearate is then screened and mixed in.

Preparation of concomitantly sprayed tableting material

Ascorbic acid, sorbitol and sweetener are dissolved in water at 40° C. at about 40% solids content and sprayed onto an identically composed bed of crystal seeds (proportion of the total mass about 15%) in a fluidizing apparatus. The spray granules are mixed with the same aroma and magnesium stearate before tableting.

Results

|  | Mechanical mixture | Concomitantly sprayed material |
|---|---|---|
| Appearance | sorbitol particles are sporadically recognizable | homogeneous, readily flowable tableting granules |
| Tableting: Amount: 500 mg Press force 20 kN | | |
| Tablet hardness: | 20 N | 160 N |
| Friability | 22% | 0.2% |
| Organoleptic sensation | tablets too soft, rough surface, (unacceptable results) | sweetly acidic vitamin C tablet having a smooth surface and |

| Mechanical mixture | Concomitantly sprayed material |
|---|---|
| | pleasant chewing properties |

What is claimed is:

1. A method for improving the flavor profile of a solid formulation which comprises one or more active substances, comprising co-spray drying said active substance(s) and at least one polyol, wherein the polyol is dissolved in water, and the active substance(s) are dissolved or suspended in a solvent, and wherein the polyol is present in an amount effective to improve the flavor profile of the solid formulation.

2. A method for improving the flavor profile of a solid formulation which comprises one or more active substances, comprising subjecting said active substance(s) and at least one polyol to fluidized-bed granulation, thereby generating a form which can be directly compressed into a solid formulation, wherein the polyol is dissolved in water, and the active substance(s) are dissolved or suspended in a solvent, and wherein the polyol is present in an amount effective to improve the flavor profile of the solid formulation.

3. The method of claim 1, further comprising compressing into a solid formulation.

4. The method of claim 1, wherein the polyol is a carbohydrate.

5. The method of claim 1, wherein the solid formulation further comprises an additional flavor improver, a color agent, or a mixture thereof.

6. A solid formulation made by the process of claim 1.

7. The solid formulation of claim 6, which is obtained by co-spraying the active substance(s) and polyol(s) in a stream of air at a temperature of 120 to 300° C.

8. The solid formulation of claim 7, which is obtained by co-spraying the active substance(s) and polyol(s) at a temperature is 140 to 190° C.

9. The solid formulation of claim 6, which further comprises a natural or synthetic sweetener, a coloring agent, or a mixture thereof.

10. The solid formulation of claim 9, wherein the sweetener is saccharin, acesulfam K, neohesperidin DC, sucralose, thaumatin or stevioside.

11. The solid formulation of claim 6, wherein the polyol is sorbitol, mannitol, lactitol, isomaltol, maltitol, erythritol or xylitol.

12. The solid formulation of claim 6, which further comprises 10 to 90% by weight of a physiologically compatible Ca, Mg, Na, K, Fe or Zn salt, a trace element, one or more vitamins, one or more bitter-tasting active substances, or mixtures thereof.

13. The solid formulation of claim 12, wherein the solid formulation comprises 25–75% by weight of said substances.

14. The solid formulation of claim 6, wherein the active substance is analgesic, antacid, antiallergic, hormone, steroid, estrogen, contraceptive, nasal decongestant, $H_1$ or $H_2$ antagonist, $\beta_2$ stimulant, vasodilator, antihypertensive, anti-infective agent, laxative, antitussive, bronchodilator agent against sore throats, fungicide, antibiotic, alkaloid, oral hypoglycemic, diuretic, cholesterol-lowering agent, or bismuth or its salts.

15. The solid formulation of claim 6, wherein the active substance is one or more pharmaceuticals in an amount of 0.1 to 70% by weight.

16. The method of claim 2, further comprising compressing into a solid formulation.

17. The method of claim 2, wherein the polyol is a carbohydrate.

18. The method of claim 2, wherein the solid formulation further comprises an additional flavor improver, a color agent, or a mixture thereof.

19. A solid formulation made by the process of claim 2.

20. The solid formulation of claim 19, which is obtained by subjecting the active substance(s) and polyol(s) to fluidized-bed granulation in a stream of air at a temperature of 40 to 120° C.

21. The solid formulation of claim 19, which further comprises a natural or synthetic sweetener, a coloring agent, or a mixture thereof.

22. The solid formulation of claim 21, wherein the sweetener is saccharin, acesulfam K, neohesperidin DC, sucralose, thaumatin or stevioside.

23. The solid formulation of claim 19 wherein, the polyol is sorbitol, mannitol, lactitol, isomaltol, maltitol, erythritol or xylitol.

24. The solid formulation of claim 19 which further comprises 10 to 90% by weight of a physiologically compatible Ca, Mg, Na, K, Fe or Zn salt, a trace element, one or more vitamins, one or more bitter-tasting active substances, or mixtures thereof.

25. The solid formulation of claim 24, wherein the solid formulation comprises 25–75% by weight of said substances.

26. The solid formulation of claim 19, wherein the active substance is analgesic, antacid, antiallergic, hormone, steroid, estrogen, contraceptive, nasal decongestant, $H_1$ or $H_2$ antagonist, $\beta_2$ stimulant, vasodilator, antihypertensive, anti-infective agent, laxative, antitussive, bronchodilator agent against sore throats, fungicide, antibiotic, alkaloid, oral hypoglycemic, diuretic, cholesterol-lowering agent, or bismuth or its salts.

27. The solid formulation of claim 19, wherein the active substance is one or more pharmaceuticals in an amount of 0.1 to 70% by weight.

28. A method for improving the flavor profile of a solid formulation which comprises one or more active substances, consisting essentially of co-spray drying said active substance(s); at least one polyol; water; optionally another solvent; optionally one or more further flavor improvers; and optionally a color agent, wherein the polyol is dissolved in water and wherein the active substance(s) are dissolved or suspended in a solvent, and wherein the polyol is present in an amount effective to improve the flavor profile of the solid formulation.

29. The method of claim 1, wherein the solid formulation has a water content of less than 1% by weight.

30. A solid formulation produced by the method of claim 29.

31. The method of claim 2, wherein the solid formulation has a water content of less than 1% by weight.

32. A solid formulation produced by the method of claim 31.

* * * * *